United States Patent [19]
Farbstein et al.

[11] Patent Number: 5,085,638
[45] Date of Patent: Feb. 4, 1992

[54] SINGLE USE DISPOSABLE SYRINGE

[76] Inventors: David Farbstein, 3 Ben-Yaccov Street, Achuza, Haifa, Israel; Miriam Ochshorn, 500 E. 63rd St., #8C, New York, N.Y. 10021

[21] Appl. No.: 291,512

[22] Filed: Dec. 29, 1988

[30] Foreign Application Priority Data

Mar. 31, 1988 [IL] Israel ............................ 85937
Jun. 7, 1988 [IL] Israel ............................ 86656

[51] Int. Cl.$^5$ .............................................. A61M 5/00
[52] U.S. Cl. ........................................ 604/110; 604/195; 604/218; 604/228; 128/919
[58] Field of Search ............... 604/110, 218, 228, 187, 604/195-198; 128/919

[56] References Cited

U.S. PATENT DOCUMENTS

| | | | |
|---|---|---|---|
| 3,951,146 | 4/1976 | Chiquiar-Arias | 604/110 |
| 4,493,703 | 1/1985 | Butterfield | 604/110 |
| 4,657,028 | 4/1987 | Rich et al. | 128/765 |
| 4,699,614 | 10/1987 | Glazier | 604/110 |
| 4,713,056 | 12/1987 | Butterfield | 604/110 |
| 4,775,363 | 10/1988 | Sandsdalen | 604/110 |
| 4,775,364 | 10/1988 | Alles | 604/110 |
| 4,826,483 | 5/1989 | Molner | 604/110 |
| 4,863,427 | 9/1989 | Cocchi | 604/110 |
| 4,874,372 | 10/1989 | McArthur et al. | 604/110 |
| 4,878,899 | 11/1989 | Plouff | 604/110 |
| 4,883,466 | 11/1989 | Glazier | 604/110 |
| 4,908,020 | 3/1990 | Pattersen | 604/110 |
| 4,911,695 | 3/1990 | Lindner | 604/228 |
| 4,923,443 | 5/1990 | Greenwood et al. | 604/110 |
| 4,929,231 | 5/1990 | Pawlikowski | 604/110 |
| 4,932,941 | 6/1990 | Min et al. | 604/110 |
| 4,950,243 | 8/1990 | Estruch | 604/110 |
| 4,969,884 | 11/1990 | Yum | 604/892.1 |
| 4,973,309 | 11/1990 | Sulton | 604/110 |
| 4,978,339 | 12/1990 | Labouze et al. | 604/110 |
| 4,979,943 | 12/1990 | Trenner | 604/110 |

FOREIGN PATENT DOCUMENTS 0340899 11/1989 European Pat. Off. ............ 604/110
8802640 5/1988 World Int. Prop. O. .......... 604/110

Primary Examiner—C. Fred Rosenbaum
Assistant Examiner—Mark O. Polutta
Attorney, Agent, or Firm—Toby H. Kusmer

[57] ABSTRACT

A syringe comprising means making it possible to make the plunger integral with the end of the plunger stem during the first filling, and to cause the disconnection between these element during a refilling attempt.

12 Claims, 3 Drawing Sheets

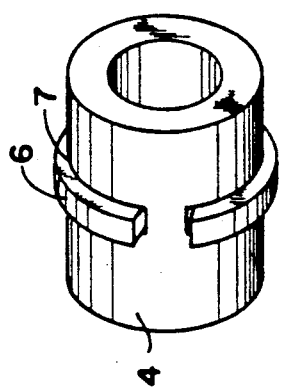
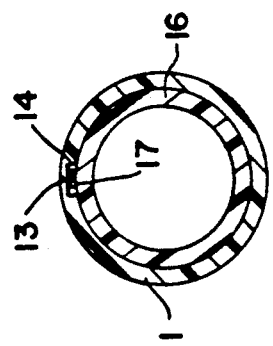
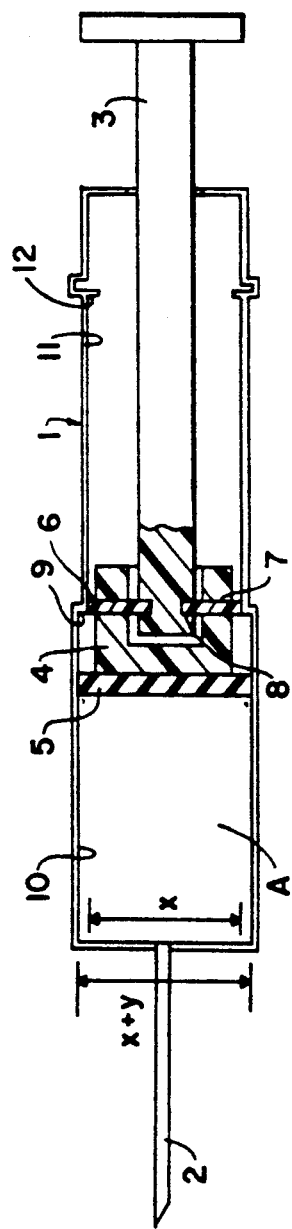
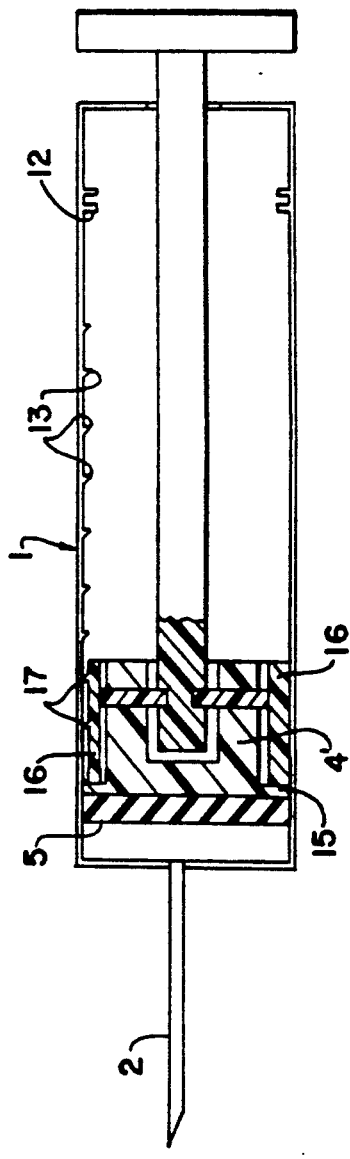

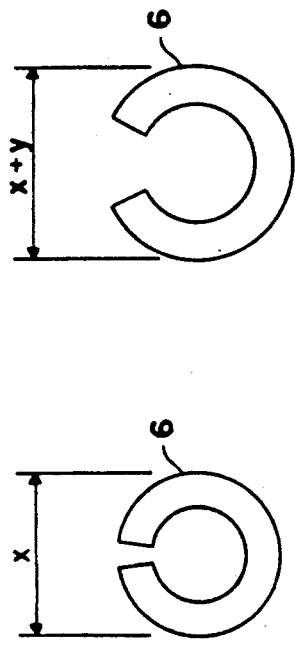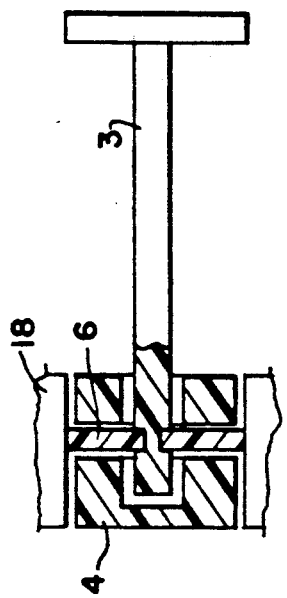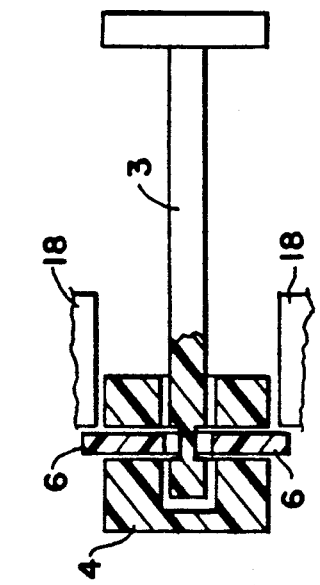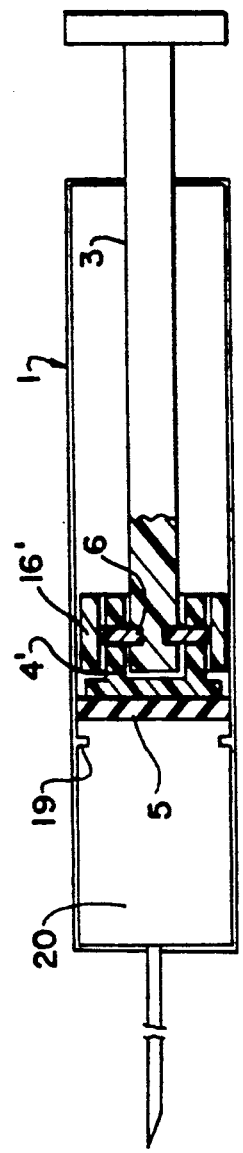

SINGLE USE DISPOSABLE SYRINGE

FIELD OF THE INVENTION

The present invention relates to a disposable syringe, and specifically to a syringe which can be used only one time since the plunging mechanism is permanently disengaged after one injection.

BACKGROUND OF THE INVENTION

Disposable syringes are now commonly used in hospitals and by the medical profession in general. These syringes are inexpensive.

In recent years with the widespread use of drugs and the availability of such inexpensive syringes there has arisen a serious problem when these syringes are used by numerous people, i.e. transferred from one person to another which can spread infectious diseases. The problem has become particularly acute with the advent of AIDS.

SUMMARY OF THE INVENTION

It is the object of the present invention to provide a simple and inexpensive disposable syringe for mass use by the medical profession which cannot be re-used once the initial single injection has been given.

It is a further object of the invention to provide a syringe with a hypodermic needle which is retractable into the syringe body after injection, thereby preventing inadvertent pricking of persons with the contaminated needle.

In accordance with the present invention there is provided a syringe comprising a tubular housing having an entrance for a plunger at one end and an outlet for fluid at the other end, a plunger disposed in said housing and means for preventing the plunger from drawing liquid into the syringe once the plunger has been pushed in the ejecting direction.

In a preferred embodiment, the plunger comprises a piston and piston rod releasably coupled to one another, and further comprising means for holding said piston and piston rod in an engaged position when initially drawing liquid into said syringe and for releasing said piston rod from said piston once the piston is pushed forward in a manner whereby the piston rod can push the piston forward but cannot pull it backwards.

BRIEF DESCRIPTION OF THE DRAWINGS

The invention will be further understood and appreciated from the following detailed description taken in conjunction with the drawings in which:

FIG. 1 is a sectional illustration of a disposable syringe constructed and operative in accordance with the present invention;

FIG. 2 is an isometric view of a detailed of the syringe of FIG. 1;

FIG. 3 is a sectional illustration of a disposable syringe constructed and operative in accordance with an alternate embodiment of the present invention;

FIG. 4 is a detail cross-sectional view of alternative decoupling means operative in the syringe of FIG. 3;

FIGS. 5a and 5b are schematic illustrations of the operation of the syringe of the present invention with piston and piston rod in respective coupled and uncoupled orientations;

FIGS. 6a and 6b are detail illustrations of elements of FIGS. 5a and 5b respectively;

FIG. 7 is a sectional illustration of a disposable syringe constructed and operative in accordance with another embodiment of the invention;

DETAILED DESCRIPTION OF THE DRAWINGS

Figure 8A:
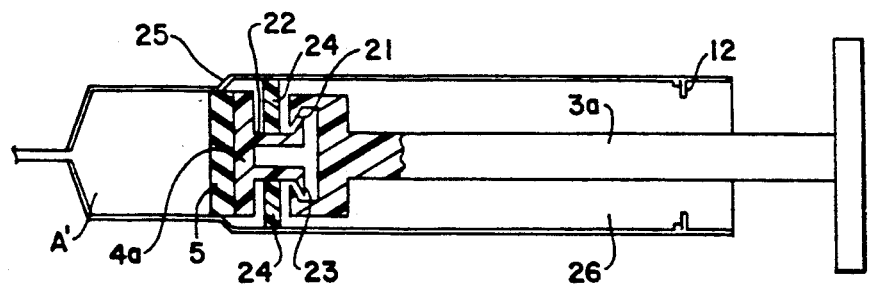
FIG. 8a is a sectional illustration of a disposable syringe constructed and operative in accordance with an alternate embodiment of the invention before use.

The present invention relates to a disposable syringe comprising a syringe body or housing, a plunger disposed within the syringe body, and means for preventing the piston from drawing liquid into the syringe once it has ejected liquid therefrom. According to a preferred embodiment, the plunger comprises a piston head releasably coupled to a piston rod, and the plunger is prevented from being used for more than a single injection by means for uncoupling the piston rod from the piston head after ejection of material from the syringe.

With reference to FIG. 1 there is shown a sectional illustration of a disposable syringe constructed and operative in accordance with an embodiment of the present invention and comprising a generally tubular housing or syringe body 1 with associated needle 2. Syringe body 1 and needle 2 may be integrally formed or needle 2 may be detachable from body 1, as known.

Disposed for slidable movement within housing 1 is a plunger comprising piston rod 3 to which is releasably coupled a piston head 4. Affixed to piston head 4 is a rubber disk 5 which contacts the liquid to be injected and creates a vacuum within the forward section A of the syringe when drawn back, as known per se.

Piston rod 3 is releasably coupled to piston head 4 as by means of a spring washer 6, which is illustrated in detail in FIGS. 6a and 6b. Spring washer 6 is arranged to be seated within a circumferential groove 7 about the piston head 4, as shown in FIG. 2. When spring washer 6 is compressed to diameter x from without, it seats within groove 7 and extends into a circumferential groove 8 in piston rod 3, which is in registration with groove 7 in the orientation of FIG. 1, the orientation for drawing liquid into the syringe. As will be explained in detail hereinbelow, when spring washer 6 is not compressed, it expands to its natural diameter x+y, thereby becoming disengaged from groove 8 and releasing piston rod 3 from piston head 4.

In the embodiment of FIG. 1, reuse of the syringe is prevented by the shape of housing 1. Part way along its length, housing 1 defines a shoulder 9 such that the circumference of housing portion 0 of syringe section A adjacent the needle 2 is larger than the circumference of the portion of housing 1 beyond shoulder 9. As can be seen, the circumference of the latter housing portion is such as to compress spring washer 6 to seat fully within piston head groove 7 and piston rod groove 8, thus engaging piston rod 3 to piston head 4. Rubber disk 5 makes a relatively tight fit with the tubular housing 1, creating a vacuum for intake of liquid and enabling ejection of same.

It will be appreciated that the size of shoulder 9 is such that the diameter of housing portion 10 is large enough to permit the expansion of spring washer 6 and concomitant disengagement from piston rod 3.

According to a preferred embodiment, stop means 12 may be provided to prevent the removal of the piston from the syringe body 1. Stop means 12 may comprise stop members extending into the body of the housing 1, or any other means for preventing the withdrawal of the piston rod 3 or piston head 4 beyond a certain point.

Referring now to FIG. 3, there is shown a sectional illustration of a disposable syringe constructed and operative in accordance with an alternate embodiment of the present invention. Like elements in FIG. 1 have the same reference numerals and will not be described again.

In this embodiment, the syringe body or housing 1 is of constant diameter and defines a plurality of inwardly extending teeth or step elements 13. According to the embodiment of FIG. 3, the teeth 13 extend inwardly from the inner wall of the housing 1. Alternatively, as shown in FIG. 4, the teeth 13 may be disposed within a channel 14 defined in the wall of the syringe body 1.

Piston head 4' defines a flange 15 at the end thereof which engages rubber disk 5. Seated about piston head 4' and movable together therewith by means of flange 15 is a cylindrical sleeve 16. Sleeve 16 defines a plurality of projecting teeth 17 on its outer surface which act in cooperation with teeth 13. Teeth 17 and 13 are such as to permit free movement of sleeve 16 in a rearward direction in syringe body 1, in order to fill the syringe with liquid, and engage one another to prevent forward movement of sleeve 16 when piston rod 3 is pushed forward to inject the liquid.

It will be appreciated that teeth 13 and 17 may be angled as illustrated, or one toothed part may comprise protruding stop members and the other may be inside grooves in which the stop members are engaged, or any other alternate arrangement which permits movement of sleeve 16 in one direction only within the syringe body 1.

The operation of the syringe of the present invention will now be described with reference to FIGS. 5a, 5b, 6a and 6b. In FIG. 5a, the syringe is shown in the filling orientation when liquid is drawn into the syringe. In this orientation, piston head 4 is coupled to piston rod 3 by spring washer 6. Spring washer 6 is compressed, as shown in FIG. 6a, by element 18, which may be the cylindrical housing of the syringe itself, as described above with reference to FIG. 1, or it may be an internal cylindrical sleeve 16 as described with reference to FIG. 3, or any other suitable means. In this compressed orientation, the piston head 4 can be withdrawn to the desired extent to fill the syringe with the required amount of medication.

When it is desired to inject the liquid medication into the patient, the piston rod 3 is pushed forwards, as in conventional syringes. When the spring washer 6 passes beyond the portion of the syringe which confines it to its compressed state, the washer 6 expands, as shown in FIGS. 5b and 6b. This occurs when the spring washer 6 passes the shoulder 9 in the syringe body of FIG. 1, or passes the sleeve 16 engaged by teeth 13 of FIG. 3, or is released in any other fashion.

Expansion of spring washer 6 causes it to disengage from the groove 8 in piston rod 3, thereby uncoupling piston rod 3 from piston head 4 (FIG. 1) or 4' (FIG. 3). It will be appreciated that in this uncoupled state, the piston head 4 can continue to be pushed by the piston rod 3 in order to eject the material from the syringe.

However, drawing the piston rod 3 backwards in an attempt to refill the syringe will result in the piston rod 3 alone being pulled free from the piston head 4 or 4', the latter remaining essentially stationary in its position inside the syringe body. Thus, the syringe can be used for one injection only, since the plunger will come apart upon any attempt to refill the syringe.

FIG. 7 shows yet another embodiment of the invention similar to that of FIG. 3. This embodiment shows alternate means for disengaging the piston rod 3 from the piston head 4'.

As can be seen, syringe body or housing 1 is of constant diameter. A pair of depending stop members 19 are provided on the interior surface of the syringe body, extending into the medication receiving cavity 20. Slideably disposed within syringe body 1 surrounding piston head 4' is a sleeve member 16'. Unlike the embodiment of FIG. 3, the outer surface of sleeve member 16' does not define teeth. Rather, sleeve member 16' is arranged to be engaged by stop members 19 as the piston rod 3 pushes the piston head 4' past the stop members 19 when ejecting liquid from the syringe.

Thus, in operation, the piston rod 3 is withdrawn to fill the syringe by vacuum. Upon ejection of the fluid from the syringe, the rubber disk 5 and piston head 4' are pushed past stop members 19, but sleeve member 16' is engaged by the stop members 19 and cannot pass. As the piston rod 3 continues to be pushed, sleeve 16' remains stationary, whereas piston head 4 continues to move forward. This causes spring washer 6 to expand, thereby releasing the piston head from the piston rod 3, as described hereinabove.

Figure 8B:
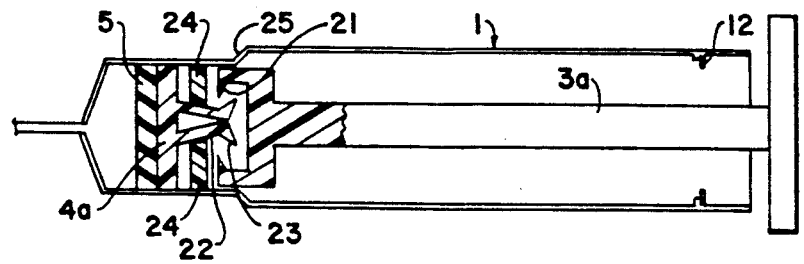
FIG. 8b is a sectional illustration of the syringe of FIG. 8a after use.

With reference to FIGS. 8a and 8b there is shown another embodiment of the present invention. This embodiment illustrates an alternate coupling of the piston rod to the piston head in the plunger.

The disposable syringe of FIGS. 8a and 8b comprises a syringe body or housing 1 including inwardly projecting stop members 12 which prevent the inadvertent removal of the plunger from the syringe before use. A plunger comprising a piston rod 3a, to which is releasably coupled a piston head 4a, is disposed for slideable movement within housing 1. Affixed to piston head 4a is a rubber disk 5.

Piston rod 3a defines at one end an inward flange 21. Piston head 4a defines a fork-like shape including two legs to engage flange 21 of piston rod 3a. Piston head 4a further defines two guide members 24, each extending from one of legs 22. Guide members 24 are arranged to slide along the internal surface of the syringe body or housing 1 during use.

Housing 1 defines a shoulder 25 partway along its length such that the circumference of housing portion A' adjacent the needle 2 is smaller than the circumference of housing portion 26 beyond shoulder 25.

Operation of the syringe of this embodiment is as follows. During the filling operation, shown in FIG. 8a, engaging flange 21. As the plunger is drawn outward, the syringe is filled with fluid, as known.

Upon ejection of the fluid from the syringe, the plunger is pushed forward until piston head 4a enters housing portion A'. As seen in FIG. 8b, in this orientation, guide members 24 force legs 22 towards one another, thereby disengaging teeth 23 from flange 21. Thus, when piston rod 3a is pulled backwards again, it is unable to pull with it the piston head 4a, which remains affixed in section A' of housing 1.

It will be appreciated that the means for coupling and uncoupling the piston head 4a from the piston rod 3a of the plunger illustrated in FIGS. 1 to 8b are not the only possible means for implementing the invention. Rather, any other method of releasably coupling the two elements during filling of the syringe and uncoupling the elements during or after injection may alternately be employed.

There is also provided in accordance with the present invention a disposable syringe including a retractable needle which can be withdrawn into the syringe body to prevent pricking of the user or medical staff after use. This is particularly important when the patient suffers from hepatitis or AIDS or other disease transmittable in this fashion. This retractable needle is preferably utilized in conjunction with the decoupling feature described with reference to FIGS. 1 to 8 to provide maximum protection for the user, but can also be utilized with conventional syringes.

Figure 9:
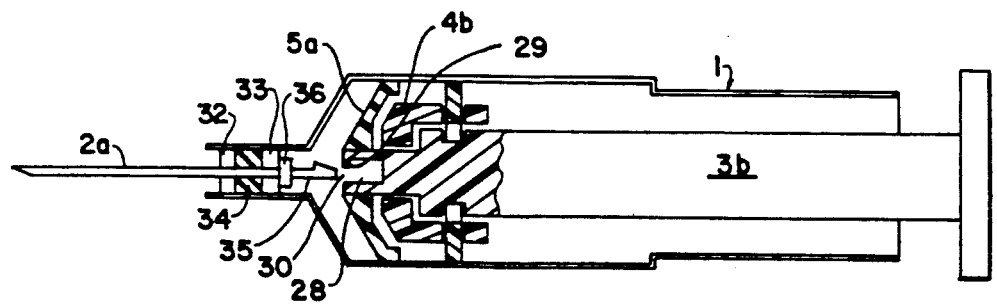
FIG. 9 is a sectional illustration of a disposable syringe constructed and operative in accordance with still another embodiment of the invention.

Referring now to FIG. 9 there is shown such a syringe comprising a syringe body 1 tapering to a needle retaining portion 2a. A plunger comprising a piston rod 3b is slideably disposed within syringe body 1 and is provided with piston head 4b with rubber disk 5a for contacting the fluid to be injected and creating the required vacuum for drawing the fluid, as known.

The forward end of piston rod 3b defines a recess 28 defining an internal should 29 whereby the interior of recess 28 is of larger diameter than the entrance 30 thereto. An hypodermic needle 2a is mounted in needle retaining portion 31 of the syringe and retained in place as by molded plastic retaining rings 32, 33. In order to prevent sliding movement of the needle 2a during injection, a tight fitting rubber plug 34 is preferably disposed between retaining rings 32 and 33 through which needle 2a passes and by which it is gripped.

Hypodermic needle 2a differs from conventional hypodermic needles in that it defines a hook member 35 at one end. It also preferably defines a stop member 36 for engaging plastic ring 33 to insure that it is not pushed out of the syringe during injection. Hook member 35 is arranged to enter recess 28 when the plunger is pushed all the way forward to eject fluid from the syringe. The hook member 35 engages shoulder 29 of recess 28 and cannot be released therefrom.

Figure 10:
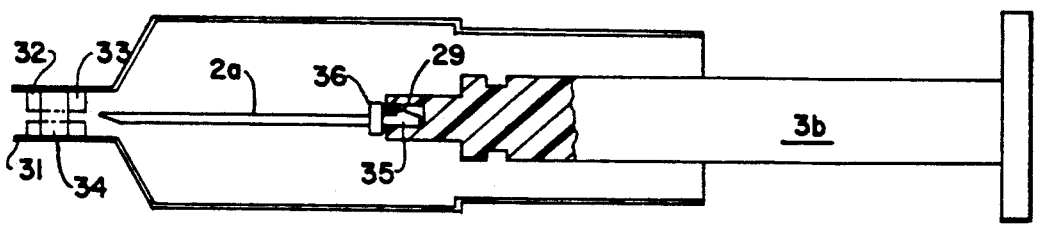
FIG. 10 is a schematic illustration of the syringe of FIG. 9 after use.

Operation of this syringe will now be described with reference to FIGS. 9 and 10. The syringe body 1 is filled with fluid, as is known, and the needle 2a is injected into the patient. The piston rod 3b is pushed forward to inject the fluid. At the end of the piston rod's forward movement, recess 28 engages hook member 35 of hypodermic needle 2a, which becomes locked to the piston rod 3b. The piston rod 3b is then pulled back until the point of needle 2a is enclosed either within rubber plug 34 or within the syringe body. The syringe may then be disposed of, thus avoiding contamination of the operator.

It will be appreciated that the operation of the syringe does not differ in the case where the piston rod of the plunger disengages from the piston head thereof. The hypodermic needle remains affixed to the piston rod while the piston head remains locked inside the syringe body.

It will be appreciated by those skilled in the art that the invention is not limited to what has been described hereinabove by way of example. Rather, the scope of the invention is limited solely by the claims which follow.

We claim:

1. A syringe comprising a tubular housing having an entrance for a plunger at one end and an outlet for fluid at the other end, a plunger disposed in said housing and movable relative to the housing between a rear position and a forward position, and means for preventing the plunger from drawing liquid into the syringe once it has been pushed to said forward position;

wherein said plunger comprises a piston and piston rod releasably coupled to one another, and means for releasably coupling said piston to said piston rod when initially drawing fluid into said syringe as said plunger is moved to said rear position and for disengaging said piston from said piston rod when ejecting fluid from said syringe as said plunger is pushed toward said forward position so that the piston rod cannot pull the piston back to draw more fluid into the syringe, said means for releasably coupling said piston to said piston rod including a spring washer circumferentially disposed about said piston rod and engaging said piston and piston rod when under radial compression and releasing said piston from said piston rod when the radial compression of the washer is released, and means for radially compressing said washer when initially drawing fluid into said syringe as said plunger is moved to said rear position and releasing the radial compression of said washer as said plunger is moved toward said forward position.

2. A syringe as in claim 1, wherein said means for radially compressing and releasing the compression of said spring washer includes a first plurality of teeth extending inwardly from an inner surface of said tubular housing and a cylindrical sleeve, disposed about the piston, for radially compressing said spring and including a second plurality of teeth protruding from an outer surface of the sleeve for engagement with the first plurality of teeth of the tubular housing; said first and second plurality of teeth being arranged to permit movement of said sleeve within the tubular housing toward said rear position and to prevent movement of said sleeve within the tubular housing from said rear position toward said forward position.

3. A syringe as in claim 2, wherein said first plurality of teeth as disposed within a channel provided in the wall of the tubular body.

4. The syringe of claim 1, further wherein said tubular housing comprises forward and rear compartments, said rear compartment having a smaller inside diameter than said forward compartment.

5. The syringe of claim 4, further wherein said spring washer is sized and configured so as to be radially compressed in said rear compartment and to released from radial compression in said forward compartment.

6. The syringe of claim 5, further within said piston comprises an opening adapted to receive the forward end of said piston rod; said piston rod comprises an annular groove adjacent said forward end, said groove being sized to receive said spring washer; and said piston additionally comprises a circumferentially-extending slot sized to receive said spring washer and positioned so as to be radially alignable with said groove when said forward end of said piston rod is received in said opening.

7. The syringe of claim 6, further wherein said spring washer is sized and configured so that when said spring washer has been compressed radially, said spring washer may be received simultaneously in said slot in said piston rod and in said groove in said piston, and so that when said spring washer is released from radial compression, said spring washer is received in only one of said slot and said groove.

8. The syringe of claim 1, further comprising a hollow sleeve with an exterior wall having a diameter less than the interior diameter of said tubular housing so as to be slidably contained therein, said tubular housing additionally comprising a first plurality of projections extending radially inwardly and sized and configured so as to restrain movement of said sleeve past said projections in at least one direction.

9. The syringe of claim 8, further wherein said spring washer is sized and configured so as to be radially compressed when inside said sleeve and to be released from radial compression when slid out of said sleeve.

10. The syringe of claim 9, further wherein said piston comprises an opening adapted to receive the forward end of said piston rod; said piston rod comprises an annular groove adjacent said forward end, said groove being sized to receive said spring washer; and said piston additionally comprises a circumferentially-extending slot sized to receive said spring washer and positioned so as to be radially alignable with said groove when said forward end of said piston rod is received in said opening.

11. The syringe of claim 1, additionally comprising a needle releasably coupled to the forward end of said housing, and retraction means for retracting said needle into said housing when said piston rod is moved a predetermined distance away from said forward end of said housing.

12. A syringe comprising a tubular housing with forward and rear compartments, said forward compartment having a smaller inside diameter than said rear compartment, said housing having an entrance for a plunger at the rear end thereof and an outlet for fluid at the forward end thereof, a plunger disposed in said housing and movable relative to the housing between a rear position and a forward position, and means for preventing the plunger from drawing liquid into the syringe once it has been pushed to said forward position; wherein said plunger comprises a piston and piston rod releasably coupled to one another, and means for releasably coupling said piston to said piston rod when initially drawing fluid into said syringe as said plunger is moved to said rear position and for disengaging said piston from said piston rod when ejecting fluid from said syringe as said plunger is pushed toward said forward position so that the piston rod cannot pull the piston back to draw more fluid into the syringe, said means for releasably coupling said piston to said piston rod comprising:

(a) first and second legs attached to said piston in spaced relation to the forward end of said piston rod so that said legs are movable between a first position wherein said legs extend parallel to one another and to the longitudinal axis of said piston rod, and a second position wherein said legs extend toward one another transversely to the longitudinal axis of said piston rod;

(b) engagement means attached to said forward end of said piston rod for engaging said first and second legs so as to couple said piston rod to said legs only when said legs are in said first position; and, (c) a spring washer circumferentially disposed about said first and second legs so as to define a central aperture wherein said central aperture has a first inside dimension when said spring washer is in the rear compartment of said housing, said first inside dimension being of a size sufficient to permit said legs to remain in said first position while positioned in said central aperture and a second inside dimension when said spring washer is in the forward compartment of said housing, said second inside dimension being of a size sufficient to accommodate said legs in said central aperture only when said legs are in said second position.

* * * * *

UNITED STATES PATENT AND TRADEMARK OFFICE
CERTIFICATE OF CORRECTION

PATENT NO. : 5,085,638

DATED : February 4, 1992

INVENTOR(S) : David Farbstein, et al.

It is certified that error appears in the above-identified patent and that said Letters Patent is hereby corrected as shown below:

Claim 3, column 6, line 45, delete "as" and substitute therefor -- are --.

Claim 5, column 6, line 53, after "to" insert -- be --.

Claim 6, column 6, line 55, delete "within" and substitute therefor -- wherein --.

Signed and Sealed this

Twenty-fifth Day of May, 1993

Attest:

MICHAEL K. KIRK

Attesting Officer

Acting Commissioner of Patents and Trademarks